(12) United States Patent
Gall et al.

(10) Patent No.: US 8,491,583 B2
(45) Date of Patent: Jul. 23, 2013

(54) INTRAMEDULLARY MEDICAL DEVICE AND METHODS OF USE AND MANUFACTURE

(75) Inventors: Kenneth A. Gall, Atlanta, GA (US); Kurt Jacobus, Atlanta, GA (US); Heidi K. Waldman, Atlanta, GA (US); Douglas Pacaccio, Alexandria, VA (US); Mark Harrold, Santa Clara, CA (US)

(73) Assignee: MedShape, Inc., Atlanta, GA (US)

( * ) Notice: Subject to any disclaimer, the term of this patent is extended or adjusted under 35 U.S.C. 154(b) by 120 days.

(21) Appl. No.: 12/919,146

(22) PCT Filed: Feb. 27, 2008

(86) PCT No.: PCT/US2008/055188
§ 371 (c)(1),
(2), (4) Date: Aug. 24, 2010

(87) PCT Pub. No.: WO2009/108194
PCT Pub. Date: Sep. 3, 2009

(65) Prior Publication Data
US 2011/0004212 A1     Jan. 6, 2011

(51) Int. Cl.
*A61B 17/58* (2006.01)
*A61B 17/66* (2006.01)
*A61B 17/68* (2006.01)

(52) U.S. Cl.
USPC .................................. 606/62; 606/63; 606/66

(58) Field of Classification Search
USPC ......................................... 606/62–67, 68, 294
See application file for complete search history.

(56) References Cited

U.S. PATENT DOCUMENTS

| | | | |
|---|---|---|---|
| 5,505,734 A * | 4/1996 | Caniggia et al. | 606/63 |
| 6,200,317 B1 * | 3/2001 | Aalsma et al. | 606/62 |
| 2005/0159749 A1 * | 7/2005 | Levy et al. | 606/72 |
| 2006/0264945 A1 * | 11/2006 | Edidin et al. | 606/63 |

* cited by examiner

*Primary Examiner* — Eduardo C Robert
*Assistant Examiner* — James Palmer
(74) *Attorney, Agent, or Firm* — Furman IP Law (57) ABSTRACT

Intramedullary medical devices (e.g., intramedullary nails) and methods for their use and manufacture are described herein. The intramedullary medical devices described herein may provide sustained compressive forces across a bone fusion site despite bone resorption processes. Through various embodiments, the intramedullary medical devices described herein may provide non-linear force curves relative to displacement. Intramedullary medical devices are described with multiple elements made of different materials. Examples of intramedullary medical devices are described with shape memory alloys.

10 Claims, 8 Drawing Sheets

INTRAMEDULLARY MEDICAL DEVICE AND METHODS OF USE AND MANUFACTURE

CROSS REFERENCE TO RELATED APPLICATION

This application is a U.S. national phase of International Patent Application No. PCT/US2008/055188, filed Feb. 27, 2008, entitled "Intramedullary Medical Device and Methods of Use and Manufacture", which is incorporated herein by reference in its entirety.

BACKGROUND

Tibio-talo-calcaneal (TTC) ankle fusion is a technique which may be used in order to achieve functional, stable, and pain-free orthopedic fusion for the treatment of appropriate medical conditions. Intentional bone fusions which are unsuccessful can lead to patient pain, recurring surgery, infection, loss of limb function, and/or, in extreme cases, limb amputation.

SUMMARY

Intramedullary medical devices (e.g., intramedullary nails) and methods for their use and manufacture are described herein. The intramedullary medical devices described herein may provide sustained compressive forces across a bone fusion site despite bone resorption processes. Through various embodiments, the intramedullary medical devices described herein may provide non-linear force curves relative to displacement. Intramedullary medical devices are described with multiple elements made of different materials. Examples of intramedullary medical devices are described with shape memory alloys.

In one aspect the disclosure describes an intramedullary medical device, including a first element with a first anchor hole adapted to accept a first bone anchor, a second element with a second anchor hole adapted to accept a second bone anchor, and a third element which is compliant to greater than about 1 percent strain without plastic deformation, wherein the third element is connected to the first element and connected to the second element.

In another aspect, the disclosure describes an intramedullary medical device, including a sleeve with a closed end, an insertion tip connected to the closed end, wherein the insertion tip includes a first through-hole adapted to receive a first bone anchor. The intramedullary medical device also includes a shape memory alloy element attached to a first interior surface of the sleeve. The intramedullary medical device also includes an anchor element attached to the shape memory alloy element, wherein the anchor element includes a second through-hole adapted to receive a second bone anchor, wherein the anchor element and the sleeve are slidably interconnected.

In another aspect, the disclosure describes an intramedullary medical device, including a proximal anchor element adapted to be fixed to a human tibia, a shape memory alloy element connected with the proximal anchor element, and a distal anchor element connected with shape memory alloy element, wherein the distal anchor element is adapted to be fixed to a human calcaneus, wherein the distal anchor element is slidably interconnected with the proximal anchor element.

These and various other features as well as advantages will be apparent from a reading of the following detailed description and a review of the associated drawings. Additional features are set forth in the description that follows and, in part, will be apparent from the description, or may be learned by practice of the described embodiments. The benefits and features will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

DETAILED DESCRIPTION

The following description of various embodiments is merely exemplary in nature and is in no way intended to limit the disclosure. While various embodiments have been described for purposes of this specification, various changes and modifications may be made which will readily suggest themselves to those skilled in the art, and which are encompassed in the disclosure.

Unless otherwise indicated, all numbers expressing quantities, measurements (e.g., strains, stresses), properties, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, will inherently contain certain errors necessarily resulting from the standard deviation found in its testing measurements.

Figure 1:
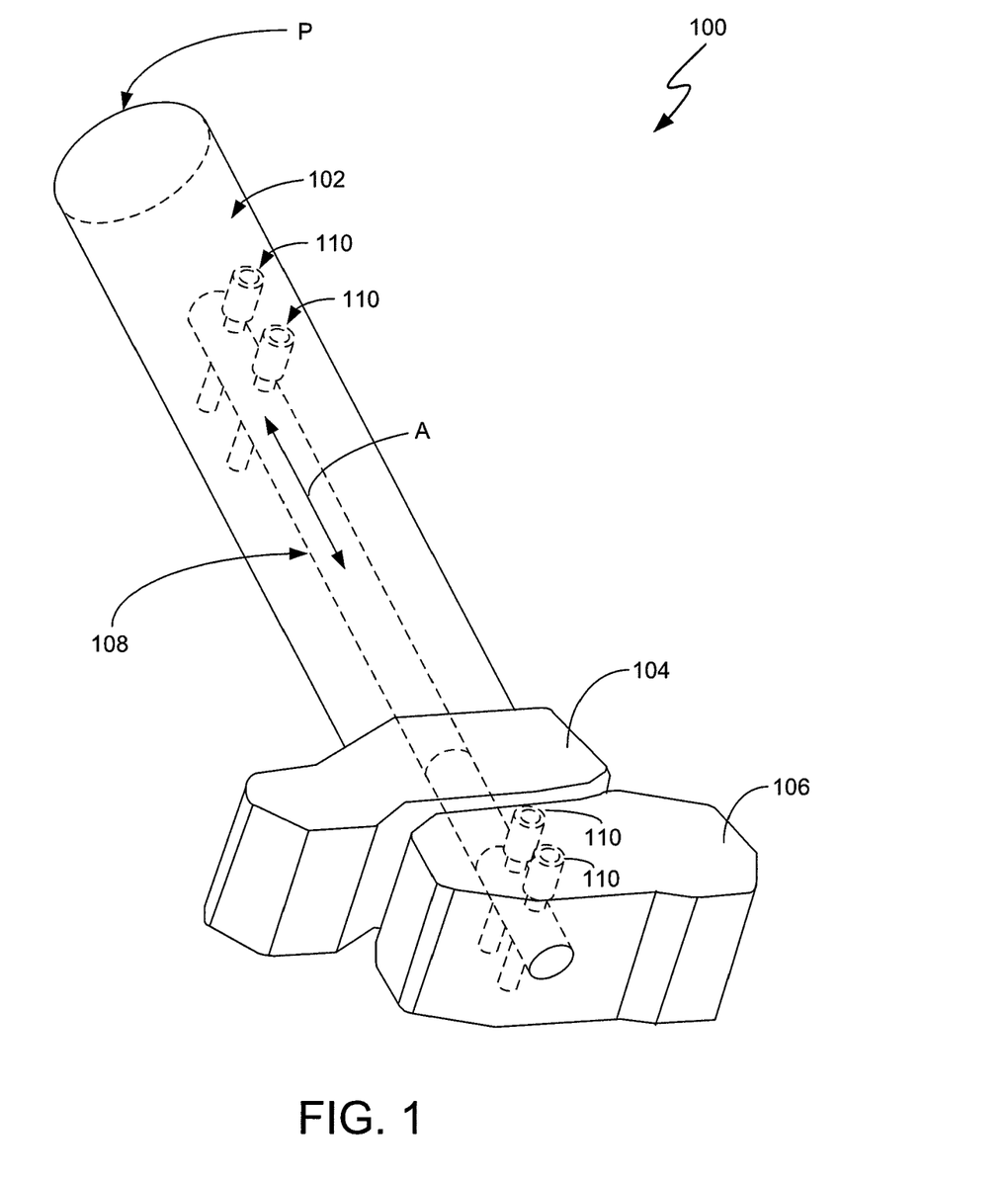
FIG. 1 shows an example use of an intramedullary device used in a TTC procedure.

FIG. 1 shows an example use of an intramedullary device used in a TTC procedure. TTC is a procedure which allows bones in the ankle of a patient to fuse over time. The tibia 102, talus 104, and calcaneus 106 are held against each other and boney in-growth between the bones is facilitated. The boney in-growth is facilitated through an intramedullary medical device 108. An intramedullary medical device 108 is positioned inside a bore created in a patient's tibia 102 (roughly along the long axis A of the tibia) and anchored proximally via a bone anchor such as a bone screw 110. The procedure may create substantially parallel bores in the patient's talus 104 and calcaneus 106, allowing the intramedullary medical device to pass through the two bones on the way to the proximal anchor site in the patient's tibia 102. Additional bone anchors (e.g., bone screws 110) may be placed in the patients calcaneus 106, thereby allowing the intramedullary device to hold the patient's tibia 102, talus 104, and calcaneus 106 under compression while the bones fuse over time. A bone anchor(s) may be placed in the patient's tibia before or after a bone anchor(s) is placed in the patient's calcaneus.

In the embodiment shown, bone anchors are placed in a medial-lateral direction in the patient's tibia and calcaneus. Bone anchors may be placed in an anterior-posterior direction, or on an angle to a medial-lateral direction and/or anterior-posterior direction. The illustration herein of bone anchors placed in a medial-lateral direction is not meant to limit the disclosure or any claim to a particular placement direction of bone anchors.

Boney in-growth is achieved over time in a TTC procedure and the process of boney in-growth may result in the interfaces between bones compressing (e.g., as old bone compacts/resorbs, as new bone is formed) thereby resulting in a shortening of the distance between bone anchors. The compressing of bone interfaces and/or shortening of distance between bone anchors may result in a loss of the compressive stress (e.g., "compression") between bones provided by the intramedullary medical device 108. A loss of compression between the bones may result in an unsuccessful or prolonged fusion time for the bones and should otherwise be avoided. The intramedullary medical device 108 described herein limits the loss of compressive stress across bone interfaces due to a shortening of distance between bone anchors and thereby provides improved opportunities for bone fusion while boney in-growth occurs.

Intramedullary medical devices may be used in applications other than TTC procedures. For example, bones in the hand or foot may be fused using an intramedullary medical device as described herein, but which has been sized and/or shaped appropriately for the smaller bones. Other bones which form joints may also be fused through suitable sizing and shaping of an intramedullary medical device described herein. As another example, vertebrae in the spine may be fused.

Fractured bones may be held or set using an intramedullary medical device. For example, a fracture in a long bone (e.g., tibia, femur, humerus, ulna) may be held or set using an intramedullary medical device, as described herein. Fractures in other bones may also be held or set. An intramedullary medical device that is used to hold or set a bone fracture may be sized and/or shaped based on the size and/or shape of the fractured bone and/or intramedullary implantation procedure used for the fractured bone. Different processes of bone growth may be facilitated through different levels of stress applied to the bones and/or fractured portions of bone. For example, bone fractures may be fused through the use compressive stresses that are different from the stresses used for fusing bones in a joint.

Compressive stress is sustained in embodiments described herein through the use of non-linear compressive or expansive elements. Examples of non-linear compressive or expansive elements include non-linear springs and materials with non-linear stress-strain behavior. For example, a shape memory alloy (SMA) material may be used to provide a non-linear stress-strain relationship. As another example, an elastomer material may be used in a compressive or expansive element.

In one embodiment, non-linear springs or other mechanical configurations may be utilized for non-linear stress/strain behaviors in compressive or expansive elements. A spring may be a non-linear spring, a linear spring, a constant-force spring, or another type of spring. The material of the spring may be a metal or other suitable material. The spring may have shape memory properties, and/or pseudo-elastic properties. The spring may be contained in a sleeve or other protective covering to limit the possibility of unfavorable interaction between the spring and rest of the intramedullary device while stretching and/or contracting of the spring occurs. For example, the spring may be encased to avoid interactions between the spring while the spring is loaded with an expansive strain and/or while the spring recovers through contraction.

Another embodiment described herein of an intramedullary medical device 108 includes an SMA used as a contracting element between proximal and distal anchor sites of a patient. The SMA may be strained past a non-linear transition in effective modulus (further described below), such that the SMA exhibits pseudo-elastic properties, including a lower effective modulus. Depending on the treatment of the SMA, the decrease in modulus after the nonlinear transition may be significant. Relative to the total force applied to the SMA to strain it past the nonlinear transition (e.g., at about one percent strain), the increase in force required to strain the SMA through to six percent strain or more may be relatively much less. Approximately, some SMAs may appear to require only a relatively constant force to be strained from the nonlinear transition to a greater strain (e.g., near a plastic deformation point).

An SMA in this strain region can exhibit pseudo-elastic properties (also referred to as "super-elastic" properties). While in this strain region, the SMA also may recover strain without showing a significant decrease in force. In other words, in an intramedullary medical device using an SMA contracting element, the SMA may recover strain with little or no decrease in applied force across the junction between the bones. Pseudo-elastic behavior of SMAs is explained further with respect to FIG. 2D.

In a TTC procedure, the proximal anchor element is anchored to the proximal anchor site in the patient's tibia. As one example, the distal anchor element is fixed to the distal anchor site (e.g., the patient's calcaneus) after the proximal anchor element has been fixed to the patient's tibia. As another example, the distal anchor element is fixed to the distal anchor site before the proximal anchor element has been fixed to the patient's tibia. The contracting element (between the proximal anchor element and the distal anchor element) holds the bones under compression while the boney in-growth and fusion process occurs. The term fixed, as used herein with relation to an element of an intramedullary medical device being fixed to a bone, refers to the attachment of the element of the intramedullary medical device being substantially attached to the bone through the use of a bone anchor or other means.

Strain may be induced into a contracting element through stretching the contracting element before both the distal anchor element and the proximal anchor element are fixed to the patient's bone(s). In the example of a TTC procedure, the recovery of the strain in the contracting element may occur while boney in-growth occurs between the patient's tibia, talus, and calcaneus. The contracting element provides compression between the tibia, talus, and calcaneus while the boney in-growth occurs, despite the decrease in distance between the proximal and distal anchor sites. The details of the recovery of strain in the contracting element are described further below. The compression which is maintained between the tibia, talus, and calcaneus increases the chances of a successful fusion between the bones.

There may be torsional and/or bending forces on the intramedullary medical device. The forces may evolve from many sources, including forces involved with the installation of the medical device, interaction between the bones while under compression, forces from the patient's movement (e.g., flexing muscles), the boney in-growth process, outside forces, stored torsional strains and/or bending strains. As illustrated by the embodiments disclosed herein, the intramedullary medical device may include features that limit the effects of these torsional and/or bending forces on the process of boney in-growth and the successful fusion of the patient's tibia, talus, and calcaneus.

As used herein with respect to the intramedullary medical device or elements thereof, certain reference terms are used. As used herein, the term "axial" refers to a vector along the long axis A of the device (as shown in FIG. 1) or an axis parallel to the axis A. As used herein, the term "radial plane" refers to a plane perpendicular to axis A, such as a plane P. As used herein, the term "torsion" refers to rotation within a radial plane. As used herein, the term "radial" refers to a vector perpendicular to and with reference to an axis A or an axis parallel to axis A. For example, a radial vector may be a vector in a particular radial plane. As used herein, the terms "bend" or "bending" refer to distortion of an element of the medical device out of alignment with axis A. For example, a portion of the medical device may be aligned with axis A before being bent, and may be aligned at an angle to axis A after being bent.

As used herein, the term "strain" (used without a qualifier) is used to refer to engineering strain, or the local axial distortion of a material divided by the length of that material along the axis of distortion. Strains as referred to herein are therefore dimensionless. The term "absolute strain" is used herein to refer to distortion expressed in units of length. Strains refer to local distortion of a material, and do not refer to a distortion between points of an element that is achieved by a mechanical arrangement (e.g., a spring). For example, a coil spring may be extended through twisting of the coil of the spring such that the total length of the coil spring is extended 10 percent (10%) or more, yet no part of the coil is strained 10 percent (10%).

Various embodiments of intramedullary devices are described below which have properties of axial compliance and rigidity in torsion and bending. The axial compliance of the intramedullary device allows strains, which are imparted before and/or during surgery, to be recovered in manners that aid bone fusion within the patient. The torsional and bending rigidity both promote bone fusion within the patient by limiting movement across the bone fusion sites.

Figure 2A:
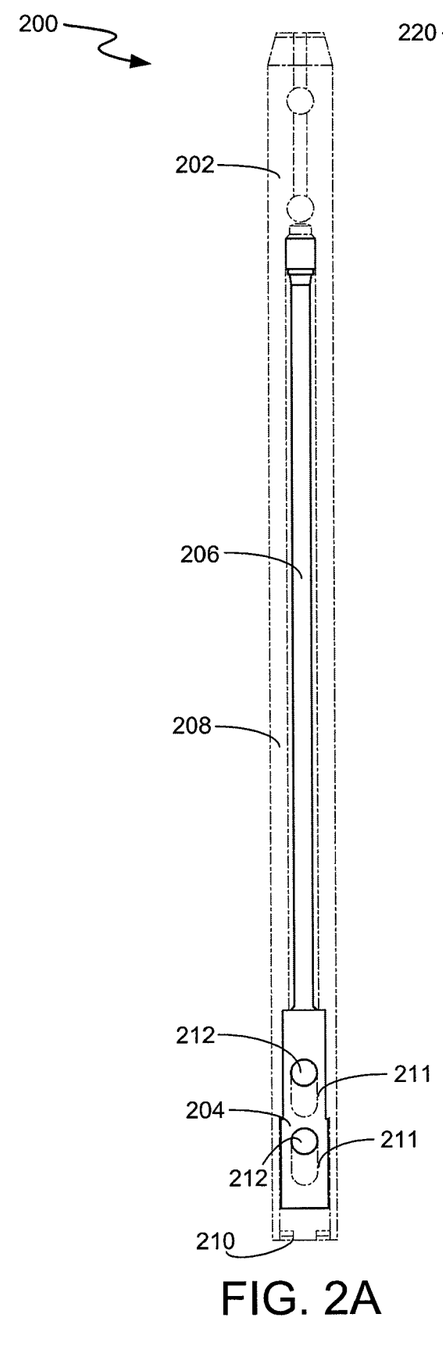
FIG. 2A shows an embodiment of an intramedullary medical device.

FIG. 2A shows an embodiment of an intramedullary medical device 200. The embodiment shown includes a proximal anchor element 202, a distal anchor element 204, a contracting element 206 which connects the anchors, and a rigid element 208 between the anchors which slidably couples the anchors. The embodiment shows the elements as assembled in the intramedullary medical device 200. Each element is discussed further below.

The rigid element 208 may slidably connect the proximal anchor element 202 and the distal anchor element 204. In the embodiment shown, the rigid element 208 is a tube-like structure that provides resistance to both torsional and bending stresses. The rigid element 208 is shown enclosing the distal anchor element 204, limiting movement of the distal anchor element to axial movement with respect to the rigid element. For example, the rigid element 208 and the distal anchor element 204 may be mated and/or slidably coupled, as described further below, such that the distal anchor element may move axially with respect to the rigid element, but may not move torsionally and/or bend (e.g., deform out of axis) with respect to the rigid element.

In the embodiment shown, the proximal anchor element 202 is connected to the rigid element 208. The proximal anchor element 202 may be attached to the rigid element 208, or the proximal anchor element may be formed with the rigid element as a single piece of material. In other words, the proximal anchor element 202 and the rigid element 208 may be portions of a single element. For example, the proximal anchor element 202 and the rigid element 208 may be portions of a single element. In another embodiment, the proximal anchor element 202 may be separated from the rigid element 208 or connected with the rigid element through a flexible interconnect.

A contracting element 206 is shown linking the distal anchor element 204 and the proximal anchor element 202. The contracting element 206 may be strained (e.g. stretched toward open end 210 of the rigid element) through sliding the distal anchor element 204. Thereby, the distal anchor element 204 may slide relative to the proximal anchor element 202 and the rigid element 208. In one embodiment, the contracting element 206 and the distal anchor element 204 are elements which may be connected. In another embodiment, the contracting element 206 and the distal anchor element 204 are both manufactured from a single piece of material.

The rigid element 208 has slots 211 disposed allowing the anchor holes 212 of the distal anchor element 204 to be accessed while the distal anchor element is slid relative to the rigid element. For example, the slots 211 may allow a bone anchor (e.g., bone screw, bone pin, rod) to pass through the rigid element 208 without causing interactions between the bone anchor and the rigid element that would axially limit the sliding of the distal anchor element 204 relative to the rigid element. The slots 211 may be designed to guide axial travel of the bone anchor while it is coupled with the distal anchor element. In the embodiment shown, the slots 211 are shown large enough for the distal anchor element 204 to be slid axially. For example, the slot 211 may guide the bone interface device to travel axially, while limiting torsional movement of the bone interface device.

The proximal anchor element 202 and distal anchor element 204 may comprise a material selected for interfacing with a bone anchor. The material of the proximal anchor element 202 may be different than the material of the rigid element 208. The material of the distal anchor element 204 may be different from the material of the contracting element 206. Each material may be selected for different properties (e.g., properties adapted for holding a screw rather than properties for contracting and/or properties for compliance along an axis).

Figure 2B:
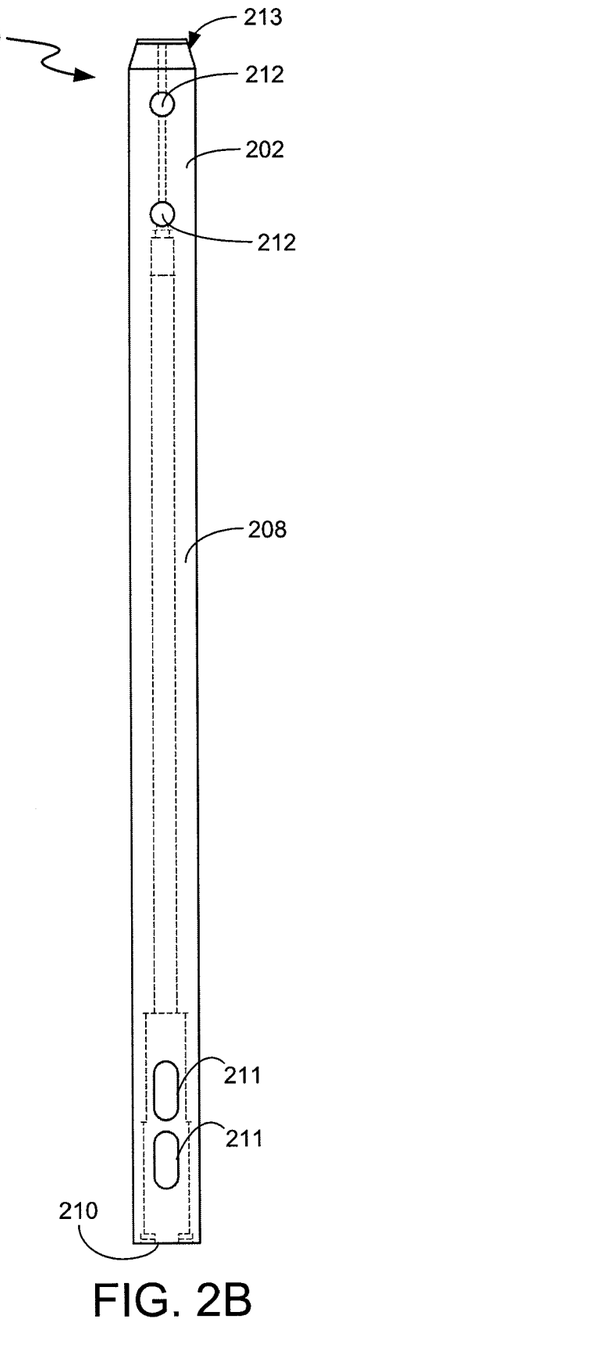
FIG. 2B shows an embodiment of a proximal anchor element attached to a rigid element of an intramedullary medical device.

FIG. 2B shows an embodiment of a proximal anchor element 202 attached to a rigid element 208 of an intramedullary medical device. In the embodiment shown, the rigid element 208 is shown generally as a tube by way of example. Other embodiments may be adapted and used wherein the rigid element 208 is a sleeve of arbitrary cross-section. For example, the rigid element 208 may be a sleeve with a rectangular cross section, or a star-patterned cross-section. As further examples, the sleeve may have a cross section that may include ridges, channels, solid regions and/or voids. The cross section of the sleeve may be adapted to achieve certain torsional resistance and/or bending resistance characteristics. In other embodiments, the sleeve structure may be replaced or buttressed by a rib, strut, and/or crutch structure. Further embodiments of rigid elements are described further below.

In the embodiment shown, the proximal anchor element 202 has a cylindrical shape with radial anchor holes 212 (e.g., perpendicular to the cylinder). In some embodiments, the end 213 of the proximal anchor element is pointed to ease insertion into a bone cavity that has been prepared in the patient's tibia. The end of the proximal anchor element 202 may be shaped in order to ease insertion, to optimize structural strength of the proximal anchor element, and/or to benefit interaction between the intramedullary device and the patient.

In the embodiment shown, the proximal anchor element 202 is attached to the rigid element 208 to form a single element 220. In another embodiment, the proximal anchor element 202 is formed together with the rigid element 208 to form a single element 220. The single element 220 as shown includes a closed end formed by the proximal anchor element 202, and an open end 210, as further described herein. Also shown and described further herein are slots 211 in the rigid element 208.

Figure 2C:
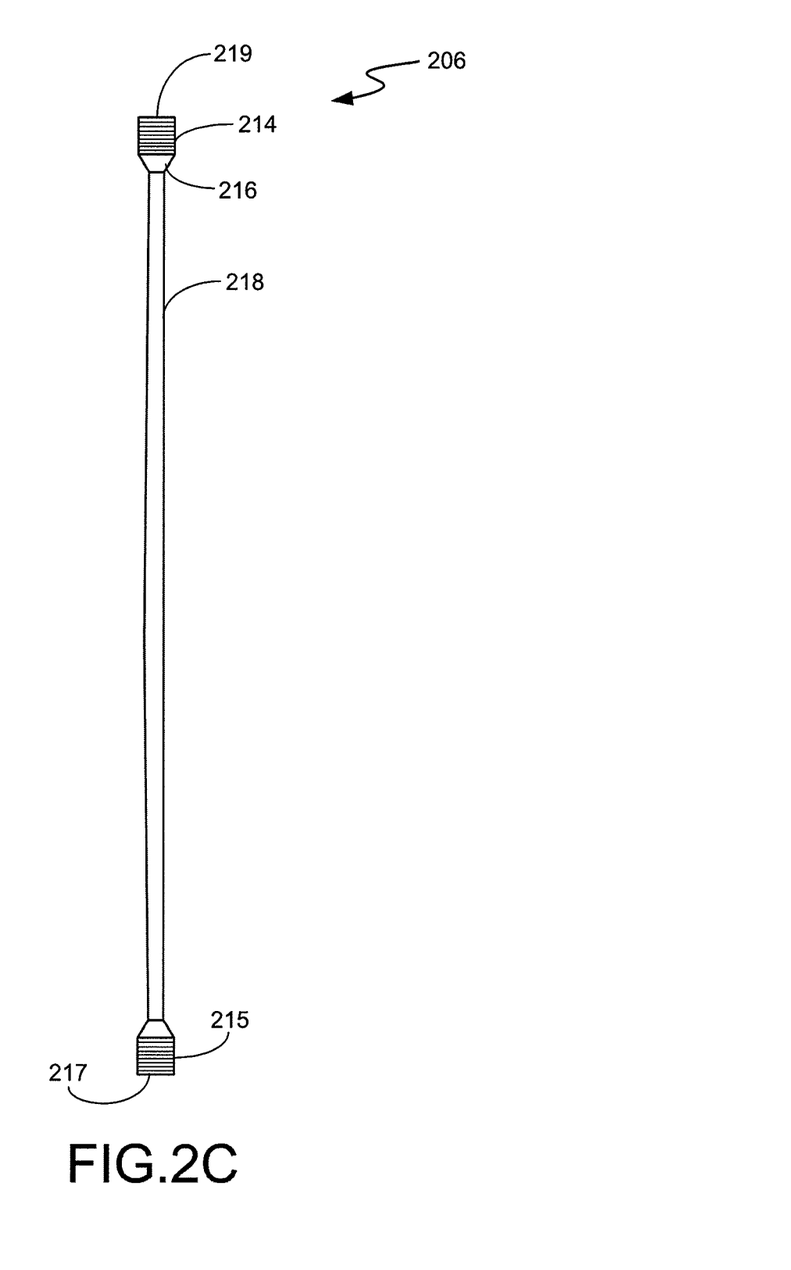
FIG. 2C shows an embodiment of a contracting element of an intramedullary medical device.

FIG. 2C shows an embodiment of a contracting element 206 of an intramedullary medical device. As described further herein, the contracting element 206 may comprise an SMA. In the embodiment shown, the contracting element 206 includes a rod of SMA. In another embodiment the contracting element 206 includes a plurality of rods of SMA. As used herein, the term "rod" is used to describe an elongate element, which may be cylindrical and may be solid. In yet another embodiment, described further below, the contracting element 206 is a tube of shape memory alloy with slots and/or voids placed in the tube. In yet another embodiment, the contracting element 206 includes a combination of rods and tubes. Other embodiments of contracting elements 206 are described herein, including other structures and/or other materials, such as linear springs, non-linear springs, and composite structures.

As further described herein, a contracting element 206 provides axial compliance between a proximal anchor element and a distal anchor element of an intramedullary medical device. As used herein, "axial compliance" refers to the capability of achieving greater than about one percent (1%) strain without plastic deformation. As used herein, "plastic deformation" refers to strain that is unrecoverable (or not otherwise recoverable under anticipated in-vivo conditions) in the absence of stress.

The SMA may be used as a contracting element 206 through straining the SMA into a pseudo-elastic state. The SMA may be treated to enhance the pseudo-elastic properties of the alloy. As described further herein with respect to FIG. 2D, the pseudo-elastic properties of an SMA may be determined to start occurring at a nonlinear transition in a stress-strain curve of the shape memory alloy. In practice, this nonlinear transition may occur between about one percent (1%) and about six percent (6%) axial strain. Other nonlinear transition regions may be developed through, for example, treatments to the SMA before, during, and/or after straining.

In the embodiment shown, the contracting element 206 has a first thread 214 on its proximal portion, which interfaces with the proximal anchor element and/or a proximal portion of the rigid element when the intramedullary device is assembled. In the embodiment shown, the contracting element 206 has a second thread 215 on its distal end, which interfaces with the distal anchor element when the intramedullary device is assembled. In an embodiment, the first and second threads 214, 215 may be threads with an opposite handedness. For example, the first thread 214 may be right-handed and the second thread 215 may be left-handed. As another example, the first thread 214 may be left-handed and the second thread 215 may be right-handed.

In one embodiment, a right-handed thread 214 is disposed on the proximal portion 219 of the contracting element 206 and the right-handed thread 214 interfaces with a right-handed thread on the proximal anchor element and/or a proximal portion of the rigid element.

The threads on the contracting element 206 may be disposed externally and/or internally. In the embodiment shown, the contracting element 206 has an external thread 214 (e.g., on the exterior of the contracting element), which engages the proximal anchor element and/or the rigid element when the intramedullary medical device is assembled. In another embodiment, the contracting element 206 may have an internal thread (e.g., on the interior of the contracting element) which engages the proximal anchor element and/or the rigid element. In another embodiment, the contracting element 206 may have both external and internal threads. For example, a contracting element 206 may have a pair of threads, one external and one internal, on a proximal portion 219 of the contracting element and the internal thread may interface with the proximal anchor element while the external thread may interface with the rigid element.

In the embodiment shown, the contracting element 206 also has an external left-handed thread 215 disposed on the distal portion 217 of the contracting element and that thread interfaces with a left-handed thread on the distal anchor element. A tool interface (e.g., hex socket, screw head) may be disposed on the distal portion 217 of the contracting element 206, allowing the contracting element to be turned. In another embodiment, the threads 214, 215 are disposed as described above, but the handedness of the threads is reversed.

In an embodiment, the intramedullary medical device may be assembled by placing a proximal portion 219 of the contracting element 206 in contact with a proximal anchor element and/or the rigid element such that respective starting portions of the threads (e.g., thread 214 and a thread on an interior surface of the proximal anchor element) are adjacent to each other. The assembly may continue with the placement of the distal anchor element in contact with the distal portion of the contracting element such that respective starting portions of the threads (e.g., thread 215 and a thread on the distal anchor element) are adjacent to each other. A locking system, as described further herein (e.g., a system of mating ridges and channels), may be engaged between the distal anchor element and the rigid element.

With the proximal thread 214 and distal thread 215 of the contracting element 206 adjacent to the respective starting portions of the threads on the other elements of the intramedullary medical device, the contracting element 206 may be turned in a clockwise direction in order to engage the contracting element with the proximal anchor element (and/or rigid element), while the same rotation will also engage contracting element with the distal anchor element. The turning of the contracting element 206, with the respective threads engaged, drives the distal anchor element closer to the proximal anchor element. Other embodiments of intramedullary medical devices, with different locking systems between elements, as described further herein, may also be adaptable to similar rotational assembly techniques.

Embodiments may be designed such that two threads disposed on different (e.g., proximal and distal) portions of the contracting element 206 need not be different handedness. For example, the proximal and distal threads 214, 215 on the contracting element 206 may be right-handed or left-handed. As another example, two threads (e.g., proximal internal thread and proximal external thread 214) may be right-handed and another thread (e.g., distal thread 215) may be left-handed.

In another embodiment, the contracting element 206 may have other locking features that engage with the other elements of the intramedullary medical device. For example, the contracting element 206 and other elements of the intramedullary medical device may interface through a locking system of cams, posts, extensions, slots, channels and/or guides. A locking system can provide the ability for one of the elements to rotate with respect to another element during assembly, and may resist the opposite rotation (e.g., including disassembly) in an opposite direction after such assembly. It should be understood that the above discussion of threads is another example of a locking system which allows rotation in one direction during assembly, and resists counter rotation (and hence, disassembly) after such assembly. Therefore, the above discussions of threads, handedness, and assembly techniques may be applied to other locking systems, including rotational locking systems, as appropriate.

In other embodiments, an expanding element is substituted for the contracting element 206. For example, the expanding element may be configured within the rigid element to cause the proximal anchor element and distal anchor element to compress the bones of the tibia, talus, and calcaneus. For example, the expanding element can "push" the distal anchor element axially with respect to the rigid element via a suitable interior configuration of the expanding element, as well as the proximal anchor element, the rigid element, and the distal anchor element.

Figure 2D:
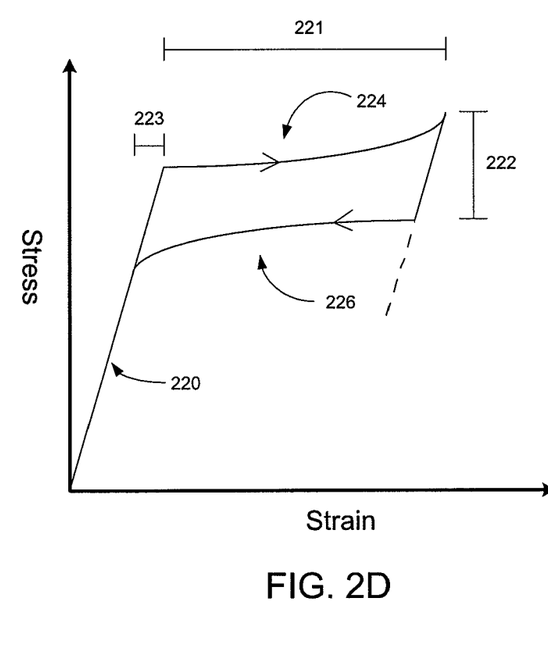
FIG. 2D shows a stress-strain curve of an example of a shape memory alloy exhibiting pseudo-elastic properties while loading and unloading strain.

FIG. 2D shows a stress-strain curve of an example of a shape memory alloy exhibiting pseudo-elastic properties while loading and unloading strain. The curve shown includes regions where the SMA displays different effective moduli. Through an initial portion of the curve 220 (the initial loading of strain on the SMA), the effective modulus of the SMA is larger than in the pseudo-elastic region of the curve 221. After the SMA is strained past a pseudo-elastic transition region 223, the SMA exhibits a smaller effective modulus. Depending on the properties of the pseudo-elastic region 221 of the SMA's stress-strain behavior, the effective modulus may be significantly less than the modulus of the initial straining of the SMA. In other words, the force exhibited resisting strain recovery and/or further straining of the SMA may be relatively constant with respect to incremental change in strain of the SMA.

The stress-strain curve shows hysteresis 222 between loading of strain on the SMA and the release of strain by the SMA, as indicated by the arrows on the curves 224, 226. In the embodiment shown, the effective moduli of the loading curve 224 and the unloading curve 226 in the pseudo-elastic region 221 of the curve are similar. However, these moduli may be different from each other in other embodiments. The unloading curve 226 shows a decrease in stress relative to the loading curve 224 through the unloading path of releasing strain. There is a significant drop in stress (indicated as hysteresis 222) exhibited by the SMA at the onset of unloading followed by a relatively constant stress section of the unloading curve 226.

An SMA with a non-linear stress-strain behavior may be used to provide relative maintenance of stress exhibited by the contracting element through a range of unloaded strain (e.g., along the unloading curve 226). For example, operation through the unloading curve 226 of the pseudo-elastic region 221 of the SMA allows the contracting element to unload strain (e.g., shorten the distance) between the proximal and distal anchor elements while maintaining a relatively constant stress between the two elements.

In some embodiments, an element of SMA may be designed and/or adapted to be in the pseudo-elastic region 221 for strains, which are utilized in the fusing of bones. A TTC procedure allows bones to fuse over time, and there may be an expected amount of travel between the bone anchors due to the bone fusion process. A contracting element made of SMA may be designed such that the expected amount of travel may be smaller than the pseudo-elastic region 221, in terms of absolute strain of the contracting element. For example, a contracting element may exhibit pseudo-elastic behavior throughout a bone fusion process if the contracting element's pseudo-elastic region 221 is exhibited over a larger absolute strain than the expected amount of travel. Some examples of absolute strain ranges corresponding to pseudo-elastic regions of contracting elements for TTC procedures may include 0 to 15 millimeters, 0 to 10 millimeters, 0 to 8 millimeters, 0 to 6 millimeters, 0 to 5 millimeters, 1 to 15 millimeters, 1 to 10 millimeters, 1 to 8 millimeters, 1 to 6 millimeters, and 1 to 5 millimeters.

Stress-strain curves similar to the curve shown in FIG. 2D may be developed for compressive strains on an SMA. The magnitude of the compressive stresses and compressive strains may differ from the tension stresses and tension strains shown in FIG. 2D. As described further herein, configurations of the proximal and distal anchor elements of the intramedullary medical device may provide compression between those elements through the stored compressive strain in a dynamic element which expands (e.g., an expansive element). In other words, recovery of the compressive strain through expansion may be configured to provide compressive forces between the proximal anchor element and the distal anchor element. As further described herein, the sustained compressive forces between the proximal anchor element and the distal anchor element provide medical advantages when used with patients (e.g., in a bone fusion application).

Figure 2E:
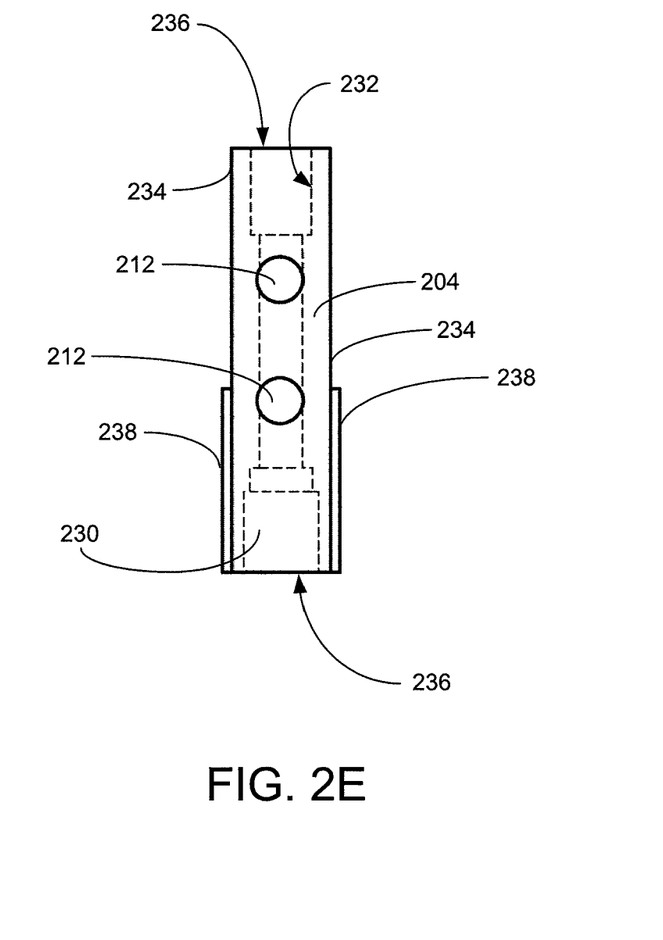
FIG. 2E shows an embodiment of a distal anchor element.

FIG. 2E shows an embodiment of a distal anchor element 204. The distal anchor element 204 includes at least one anchor hole 212. In this embodiment, the distal anchor element 204 is adapted to fit within the rigid element, as described further herein. The distal anchor element 204 may contact the rigid element along some or all of outer surface of the distal anchor element. In the embodiment shown, the distal anchor element 204 contacts the rigid element along substantially all of the outer rounded surface 234 of the distal anchor element but not the end surfaces 236. In another embodiment, the distal anchor element 204 extends beyond the rigid element. For example, other embodiments are further described below in which a significant portion of the distal anchor element 206 and/or a peripheral element is/are outside the rigid element.

Guiding and/or locking elements 238 may be included on a distal anchor element 204 which can interface with a rigid element to limit torsional movement of the distal anchor element with respect to the rigid element. The guiding/locking elements 238 may interface the distal anchor element 204 and the rigid element through a mating of ridges and channels. For example, the distal anchor element may have a ridge 238 which mates with a channel in the rigid element, thereby allowing axial movement and limiting torsional movement of the distal anchor element 204. As another example, the distal anchor element 204 may have a channel which mates with a ridge in the tube, thereby allowing axial movement and limiting torsional movement.

The ridges 238 of the distal anchor element 204 may slidably interconnect with the rigid element. The ridges 238 may allow relative movement axially (e.g., along axis A) between the rigid element and the distal anchor element 204. The ridges 238 may prevent torsional movement between the rigid element and the distal anchor element 204.

The embodiment shown includes interior threads 232 which mate to the contracting element during assembly of the intramedullary medical device. Access to the distal end of the contracting element may be provided through end surface 236 and through cavity 230 at the distal end of the distal anchor element 204. Thereby, the contracting element may be accessed in order to allow rotation (or other locking) of the contracting element to facilitate assembly, as described further herein.

Sizing or shaping of the intramedullary medical devices described herein may include bending or curving one or more elements of the device. For example, rigid elements described herein may be adapted to particular applications through being curved (e.g., fusing a joint in a curved position).

Elements of an intramedullary medical device as described herein may be rearranged and/or modified. For example, an anchor element may be expanded or reduced in size as appropriate for a particular bone. As another example, a curvature may be introduced into an element, such as a rigid element. A compressive element may be placed in a straight or curved portion of an intramedullary medical device.

Interconnections of the elements as described further herein (e.g., slidable interconnections, threads) may be positioned according to any rearrangement, and/or modification of the elements.

Figure 3A:
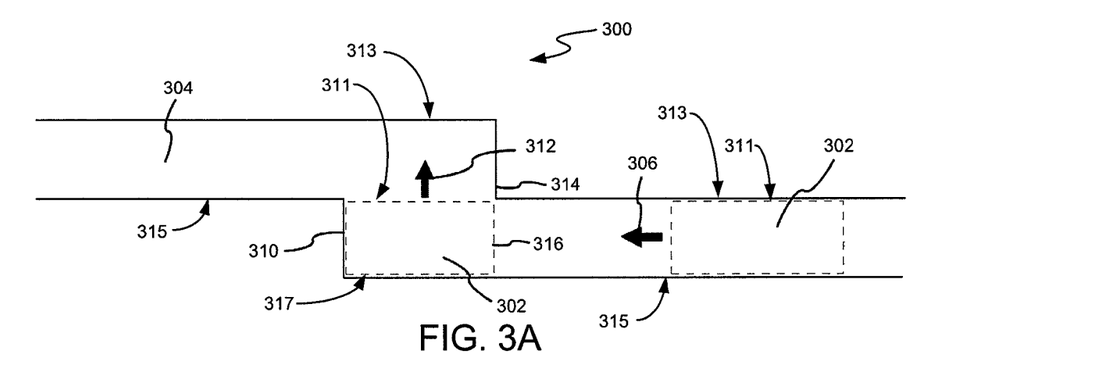
FIG. 3A shows an embodiment of a locking system including a key section and a channel which is stepped to provide a locking function.

FIG. 3A shows an embodiment of a locking system 300 including a key section 302 and a channel 304 which is stepped to provide a locking function. For example, the locking system 300 may be used to ease assembly, to assure that correct assembly has occurred, and/or to limit disassembly (e.g., through inadvertence, through mishandling).

In one embodiment, the locking system 300 is disposed between distal anchor element and the rigid element of the intramedullary medical device. As an example, a ridge on a distal anchor element may have a portion (e.g., a key section) which mates (e.g., couples, fits, interfaces with) with a portion of a channel in a rigid element. In another embodiment, as described further below with respect to FIG. 6, the locking system 300 may be disposed between the rigid element and an interface element.

During assembly of the intramedullary medical device, the dynamic element (e.g., contracting element, expanding element) may be connected after the locking system 300 is engaged. Thereby, the locking system 300 may maintain alignment of elements of the intramedullary medical device during, for example, assembly (including installation of the dynamic element), shipment, storage, insertion of the device in the patient, and/or straining of the dynamic element.

In the embodiment shown, the ridge includes a key section 302 which mates with the channel 304 through axial sliding and rotation. Initially, the key section 302 may be slid axially as shown by the arrow 306. In the embodiment shown, after the key section 302 meets a proximal axial stop 310 in the channel (so named because it limits proximal movement), the key section may be rotated 312. In other embodiments, the proximal axial stop 310 need not be reached before the rotation 312 can occur. In the embodiment shown, a distal axial stop 314 must be passed by a distal portion 316 of the key section 302 before rotation 312 can occur.

The embodiment shown limits rotational movement 312 of the distal anchor element (which includes the ridge and key section 302) relative to the rigid element (which includes the channel 304) while the ridge and channel are interfacing both before and after the ridge and channel have been rotationally mated. This limitation in relative rotational movement is accomplished through interfacing of the upper extents of the key section 311 with the upper extents of the channel 313 and/or through interfacing of the lower extents of the key section 317 with the lower extents of the channel 315. The interfacings of the extents of the ridge and channel 304 may occur both before and after the ridge and channel are rotationally mated.

Figure 3B:
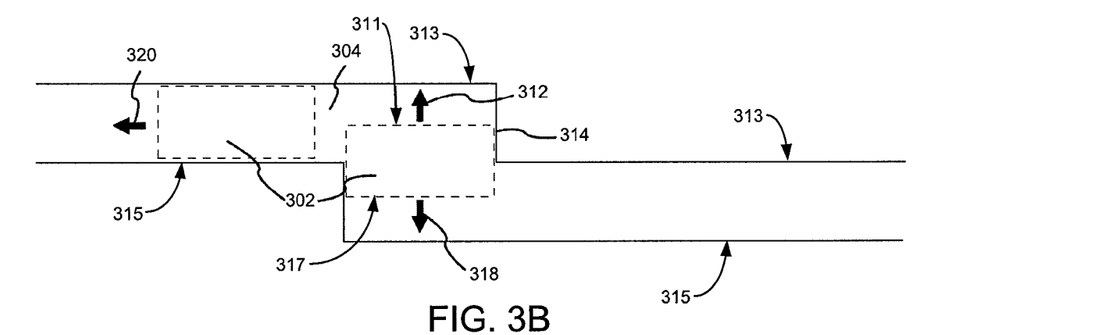
FIG. 3B shows an embodiment of a locking system including a key section and a channel with the key section rotationally locked within the channel.

FIG. 3B shows an embodiment of a locking system 300 including a key section 302 and a channel 304 with the key section rotationally locked within the channel. With the key section 302 and the channel 304 in a locked rotational position, as shown, the key section is limited from moving axially in a distal direction past the distal axial stop 314 with respect to the channel unless the key section 302 is counter-rotated 318 with respect to the channel 304. For example, the distal axial stop 314 may prevent inadvertent or unintended disassembly of the distal anchor element from the rigid element.

In the embodiment shown, at the point where the key section 302 is between the proximal axial stop 310 and the distal axial stop 314, movement is limited to rotational movement 312, 318. Rotational movement 312, 318 may occur for a determined angular rotation, as determined by the channel 304.

In the embodiment shown, during rotation the distal axial stop 314 limits axial movement of the key section 302 through interference with the distal portion 316 of the key section. Also, during rotation 312 the proximal axial stop 310 prevents further proximal axial movement until the rotation 312 is completed. After rotation 312 is completed, the key section 302 is allowed to axially move 320 further in a proximal direction. However, without counter-rotation 318, the key section 302 is limited in distal axial movement by the distal axial stop 314. Further rotational movement 312 and counter-rotational movement 318 may be limited as described above by the extents of the channel interfacing with the extents of the key section 302.

In one embodiment, counter-rotation 318 is allowed, thereby allowing the disassembly of elements (e.g., the distal anchor element, the rigid element). In another embodiment, counter-rotation 318 is limited, for example, through traps, locks, spring-loaded features. Any known manner preventing counter-rotation 318 of the key section 302 may be employed.

Figure 4:
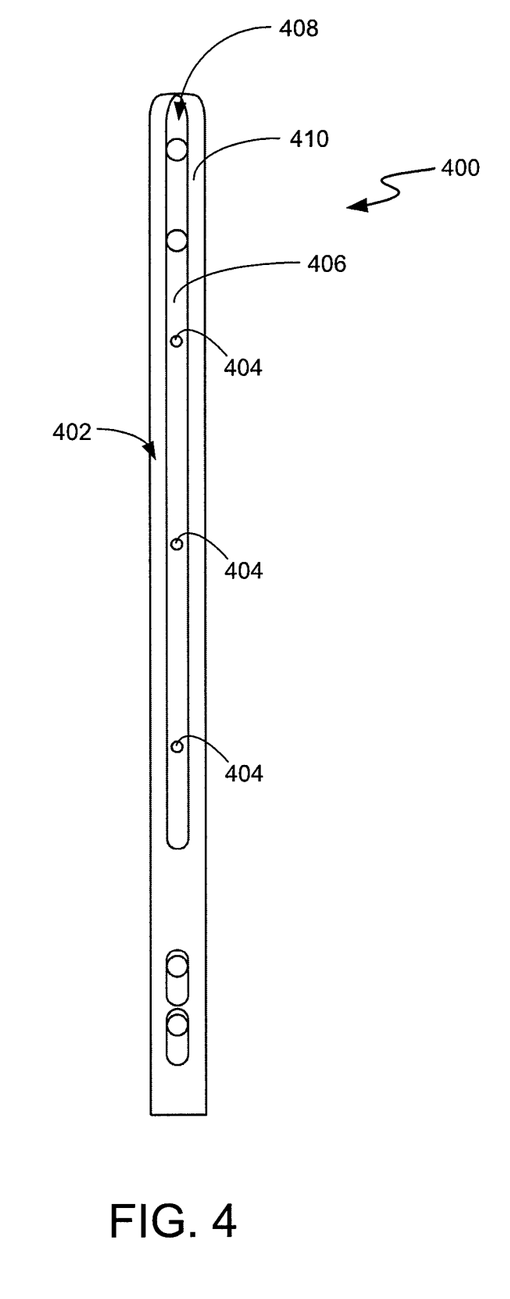
FIG. 4 shows an embodiment of an intramedullary medical device with an alternative embodiment of a rigid element.

FIG. 4 shows an embodiment of an intramedullary medical device 400 with an alternative embodiment of a rigid element 402. The rigid element shown includes openings 404 which allow bodily fluids to pass through the rigid element 402 to/from the contracting element (not shown in this view). The transit of bodily fluids may result in beneficial infection control and acceptance of the intramedullary medical device while inside the patient. The openings 404 are shown placed in a manner which maintains the rigid element's 402 resistance to torsion and bending, while still allowing fluids to transit through the rigid element 402. Other configurations of openings 404 may be used as alternatives to the illustrated configuration of openings 404.

The rigid element 402 includes a flute 406 which extends through the proximal anchor element 410 to the proximal end 408 of the rigid element. The flute 406 may be situated to guide body fluids along the flute to/from different parts of the bone bore (in which the intramedullary nail is placed within a patient) and to/from the openings 404. As further described above, the flute 404 may also be designed to strengthen the rigid element 402 through buttressing and/or variations due to the flute 406 in the cross-section of the rigid element.

Figure 5:
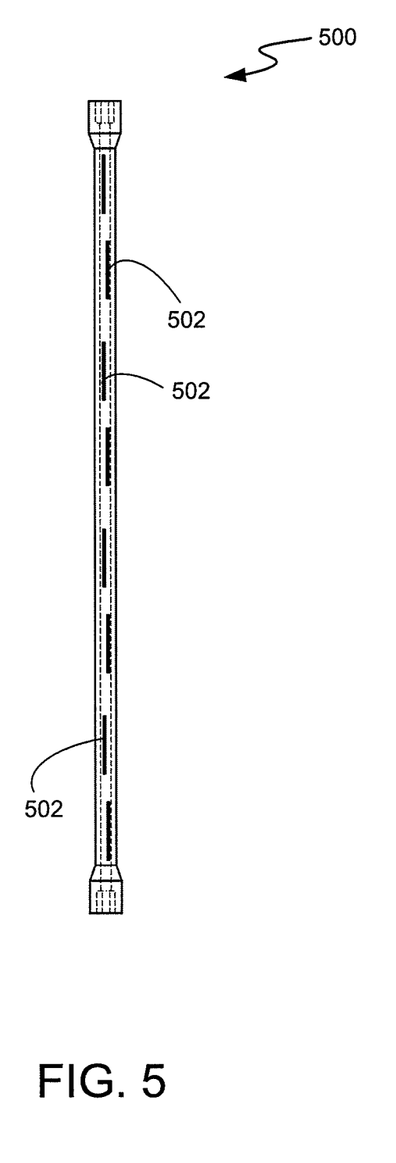
FIG. 5 shows an alternative embodiment of a contracting element for an intramedullary medical device.

FIG. 5 shows an alternative embodiment of a contracting element 500 for an intramedullary medical device. In the embodiment shown, the contracting element is a tube (e.g., composed of SMA) which has voids 502 (e.g., slots, openings) disposed in a circumferentially-spaced arrangement. The voids 502 may be designed to control the effective volume of the material of the contracting element, thereby controlling the compliance characteristics of the contracting element 500. For example, the voids 502 can reduce the effective cross-sectional area of the SMA which makes up the contracting element 500. Alternative embodiments of contracting elements are described further herein which also allow control (e.g., increasing, reducing) cross-sectional area of the SMA, for example, the use of a plurality of rods.

Figure 6:
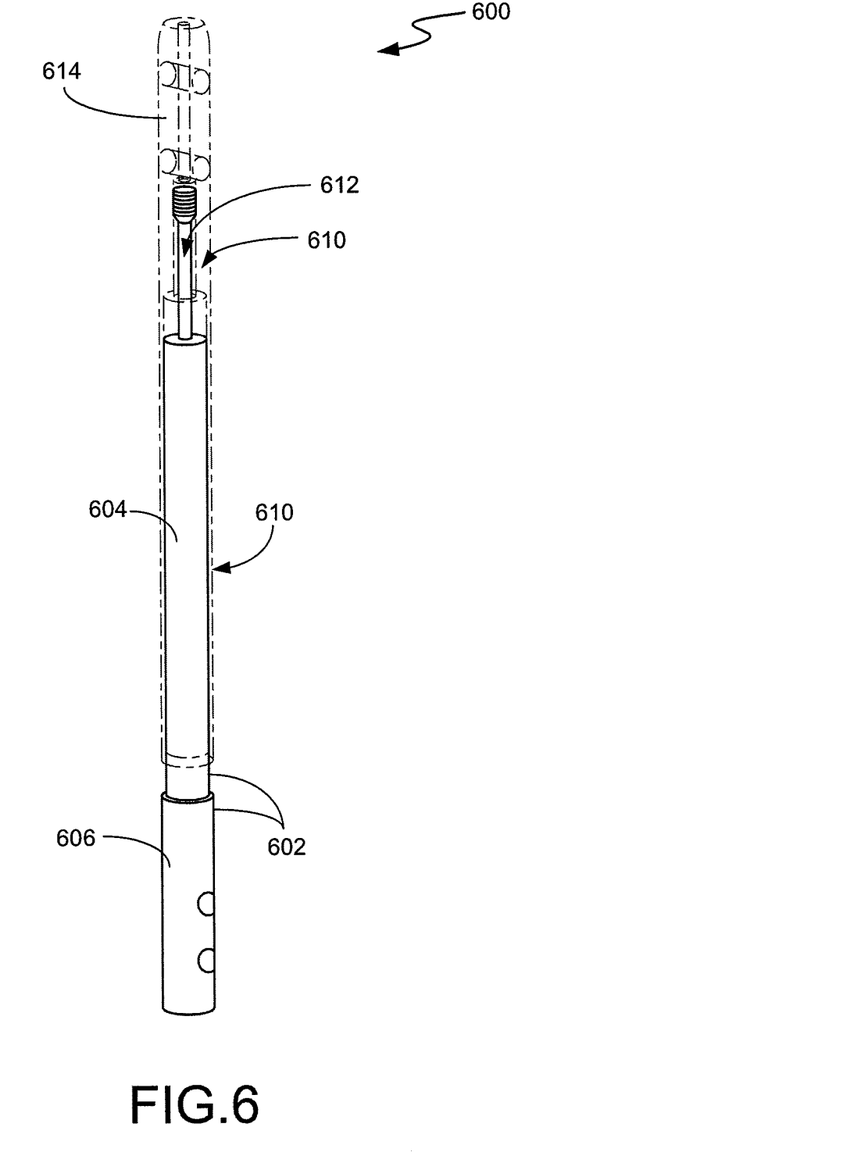
FIG. 6 shows an embodiment of an intramedullary medical device with a distal anchor element which extends outside the rigid element.

FIG. 6 shows an embodiment of an intramedullary medical device 600 with a distal anchor element 602 which extends outside the rigid element. The distal anchor element 602 may include an interface element 604 and a peripheral element 606. In the embodiment shown, the interface element 604 is partially inside a rigid element 610, and slidably interconnects with the rigid element. Slidable interconnection with the rigid element 610 is described further above with respect to further embodiments including, for example, ridges and channels. Connections between the proximal anchor element 614 and the rigid element 610 are also described above with respect to further embodiments.

In the embodiment shown, the contracting element 612 extends within the interface element 604 and attaches with the distal anchor element 602 near the connection between the interface element and the peripheral element 606. In another embodiment, the contracting element 612 attaches with the interface element 604 at or near the proximal end of the interface element.

The peripheral element 606 may flare or otherwise have a larger diameter than the interface element 604. In the embodiment shown, the interface element 604 has a smaller diameter than the peripheral element 606 to maintain a consistent outer diameter of the entire intramedullary medical device, while allowing for the thickness of the wall of the rigid element 610. Therefore, in the embodiment shown, the rigid element 610 extends only part of the way between the proximal anchor element 614 to the distal anchor site.

The peripheral element 606 contains anchor interface holes, as described further above. The anchor interface holes of the distal anchor element 602 allow the distal anchor element to be fixed to the patient's calcaneus at the distal anchor site. In the embodiment shown the peripheral element 606 is approximately situated at the distal anchor site.

In the embodiment shown, there are guiding elements between the rigid element 610 and the interface element 604 which limit torsional and bending movement. These guiding elements are described in further detail herein with respect to elements of distal anchor elements and rigid elements which perform similar functions, such as ridges and channels.

What is claimed is:

1. An intramedullary medical device adapted to provide contracting forces between a patient's bones, the intramedullary medical device comprising:
   (a) an encasement adapted to connect under compression separate bones of an ankle joint including a tibia, a talus, and a calcaneus;
      (i) wherein a proximal end of the encasement is adapted to be fixed within a medullary canal of the tibia;
      (ii) wherein a distal end of the encasement is adapted to be fixed within the calcaneus;
      (iii) wherein an intermediate portion of the encasement between the proximal the distal end is adapted to be installed within the talus;
   (b) a distal anchor element contained within the distal end of the encasement;
      (i) wherein the distal anchor element is adapted to be fixed to the calcaneus; and
   (c) a non-linear contracting element contained within the encasement;
      (i) wherein the non-linear contracting element is connected between an internal surface of the encasement and an internal surface of the distal anchor element;
      (ii) wherein the non-linear contracting element is adapted to provide compression between the separate bones of the ankle joint through moving the distal anchor element within the encasement toward the proximal end of the encasement;
      (iii) wherein the non-linear contracting element comprises a shape memory alloy adapted to exhibit a pseudo-elastic stress-strain response over a pseudo-elastic range of expansive strain imparted to the non-linear contracting element based on the distal anchor element being moved distally with respect to the proximal anchor element;
      (iv) wherein the non-linear contracting element is further adapted to hold the separate bones of the ankle joint in direct contact and under compression through the encasement, the distal anchor element, and the proximal anchor element, while the non-linear contracting element provides compressive forces via the pseudo-elastic stress-strain response of the shape memory alloy as a result of the expansive strain imparted on the shape memory alloy.

2. The intramedullary medical device of claim 1, wherein the encasement include a unitary exterior surface adapted for interfacing with the separate bones of the ankle joint.

3. The intramedullary medical device of claim 1, (i) wherein the distal anchor element has a distal bone screw interface disposed within the encasement;
   (ii) wherein the encasement includes an access port positioned outside the distal bone screw interface;
   (iii) wherein the access port is adapted such that the distal bone screw interface may be accessed in configurations of the non-linear contracting element having the pseudo-elastic range of expansive strain; and
   (iv) wherein the non-linear contracting element is adapted such that the first pseudo-elastic range of expansive strain provides through the encasement compressive forces between the separate bones of the ankle joint.

4. The intramedullary medical device of claim 3, wherein the access port is further adapted to restrict access to the distal bone screw for configurations of the non-linear contracting element that provide through the encasement expansive forces between any two of the separate bones of the ankle joint.

5. The intramedullary medical device of claim 1, wherein the distal anchor element is adapted to allow direct access to the non-linear contracting element through the distal anchor element.

6. The intramedullary medical device of claim 1, wherein the pseudo-elastic range of expansive strain is greater than an expected amount of compression between the distal anchor element and the proximal anchor element during a fusion process of the separate bones of the ankle joint.

7. The intramedullary medical device of claim 1, wherein the shape memory alloy is further adapted to comprise only either an austenite crystalline phase or a rhombohedral crystalline phase before the distal anchor element is moved within the encasement.

8. The intramedullary medical device of claim 1, wherein the shape memory alloy is further adapted not to contain a martensite crystalline phase before the distal anchor element is moved within the encasement.

9. The intramedullary medical device of claim 1, wherein the pseudo-elastic range of expansive strain is between about one millimeter absolute strain and about an eight millimeter absolute strain.

10. The intramedullary medical device of claim 1, wherein the non-linear contracting element is adapted to exhibit a non-linear engineering stress-strain response above about 1 millimeter of absolute strain.

* * * * *